Figure 1:
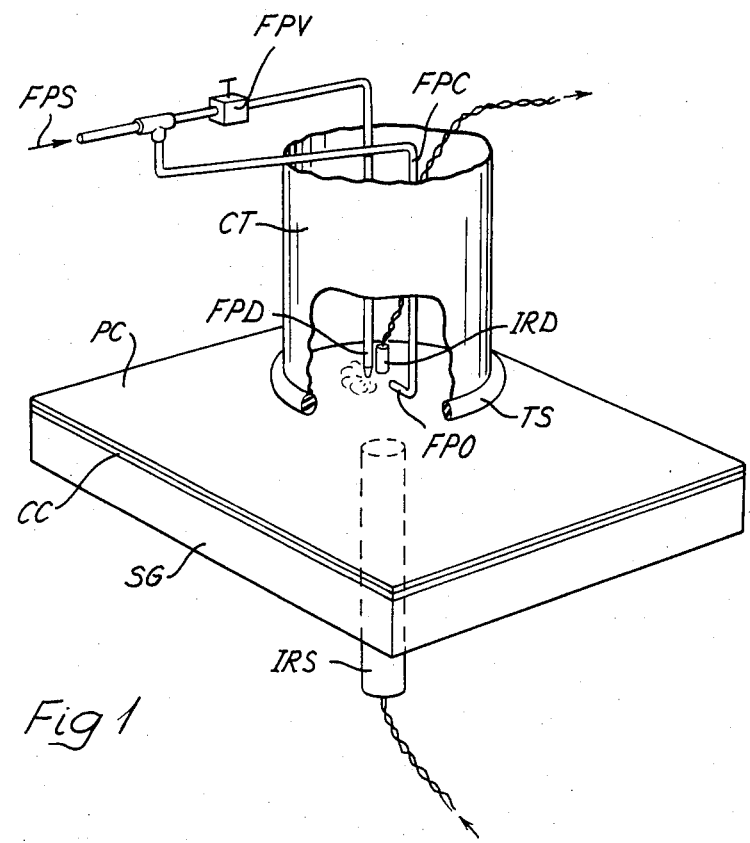

United States Patent [19]

Binns et al.

[11] Patent Number: 4,704,297
[45] Date of Patent: Nov. 3, 1987

[54] ASSESSING POWDER COATINGS

[75] Inventors: Ian D. Binns, Glasgow; Brian Makin, Dundee, both of Scotland

[73] Assignee: National Research Development Corporation, London, England

[21] Appl. No.: 822,412
[22] PCT Filed: May 8, 1985
[86] PCT No.: PCT/GB85/00193
  § 371 Date: Dec. 31, 1985
  § 102(e) Date: Dec. 31, 1985
[87] PCT Pub. No.: WO85/05182
  PCT Pub. Date: Nov. 21, 1985

[30] Foreign Application Priority Data

May 8, 1984 [GB] United Kingdom ............... 8411673

[51] Int. Cl.$^4$ .............................................. B05D 1/04
[52] U.S. Cl. ........................................ 427/9; 118/712; 427/10; 73/150 R
[58] Field of Search .................. 118/712; 427/9, 10; 73/150 R, 150 A

[56] References Cited

U.S. PATENT DOCUMENTS 2,773,412 12/1956 Huck .......................... 118/712 X
4,276,767 7/1981 Cartwright ....................... 73/7
4,301,764 11/1981 Campion ........................ 118/312
4,393,699 7/1983 Seiler ......................... 73/150 A
4,417,478 11/1983 Jon et al. ....................... 73/801

FOREIGN PATENT DOCUMENTS 0004615 10/1979 European Pat. Off. .
788223 6/1954 United Kingdom .
810862 3/1959 United Kingdom .
1556375 11/1979 United Kingdom .
2060868 5/1981 United Kingdom .

OTHER PUBLICATIONS

Technisches Messen, vol. 49, nr. 11, 1982 (Munchen, DE), C. Linhart et al.: "Beruhrungslose Bestimmung der Dicke von Oberflachenbeschichtungen durch thermische Messverfahren", pp. 391–398, see p. 397, part 4.

Primary Examiner—Shrive P. Beck
Attorney, Agent, or Firm—Cushman, Darby & Cushman

[57] ABSTRACT

A technique for assessing electrostatically deposited coatings of powder to be later fused into a surface finish. Powder deposited by the coating process onto a test piece or an unimportant part of an actual article is disturbed by, for example, a series of puffs of compressed air. The removal of the powder by the disturbance is monitored. In one arrangement infra-red light is shone through the coating and the change in transmissivity with each puff of air is measured to give an indication of the quality of the powder deposit.

14 Claims, 2 Drawing Figures

ASSESSING POWDER COATINGS

This invention relates to the assessment of the coating of a surface with a powder and more particularly, but not exclusively, the efficiency with which an electrostatic technique applies an insulating polymeric powder coating for subsequent fusing on a surface.

The technique of depositing a coating of powder on a surface by means of electrostatic force is well-known and widely used to deposit coatings of various materials such as epoxy, polyester, polycarbonate, polypropylene, nylon, and combinations of these materials, for subsequent fusion by heating. However the coating process is not easy to control except by trial and error methods which themselves are not always consistent in their results when applied in apparently identical circumstances.

It is an object of the invention to assess the coating of a surface with a powder to provide information about the coating action to assist in its control and mitigate the problems of the uncertain nature of the process at present.

According to the invention there is provided an apparatus for destructive assessment of a particulate coating including means to apply radiation to a deposited particulate coating and means to measure the radiaton passed through the coating, means to disturb a small region of the particulate coating in a reproducible manner, means to measure the radiation passed through the disturbed coating, and means to determine the change in the radiation transmissibility of the deposited particulate coating as a result of the disturbance whereby an indication of the effect on the coating of the reproducible disturbance is provided as an indication of the adherence of the coating and the efficiency or otherwise and the deposition of the coating.

The apparatus may include means to repeat the disturbance at the already disturbed coating to permit a further such determination.

Specifically the apparatus may include a conductive surface connectable to ground and to which a coating of powder may be applied by electrostatic means, fluid pressure means to disturb a small region of the coating, means to send infra-red radiation through the coating and the surface, and any support therefor, to measure the change in the transmissivity of the coating resulting from the disturbance.

The conductive surface may be a metallic coating on a glass support to form a test piece.

The means to disturb the coating may be a fluid pressure duct, such as a hypodermic needle, surrounded by a housing sealable to a coating and provided with a controllable source of fluid pressure, such as compressed air suppliable in bursts of set time and pressure. The means to detect radiation may be a solid-state detector of infra-red radiation associated with the fluid pressure duct. The means to apply radiation may be an opposed source of said radiation. The radiator and detector may be interchanged.

The apparatus may be arranged to pass the radiation normally or at another angle through the coating and any supporting surface and substrate, which are radiation-transmissive. The radiation may be reflected, to pass twice through the coating for measurement, for an opaque substrate or supporting surface.

The radiation may be other than infra-red, for example in the form of microwaves or from radio-active decay, such techniques being well-known in the art for measuring material thickness.

According to the invention there is provided a method of assessing a particulate coating including applying a coating to a surface, permitting or causing radiation to pass through the coating and measuring the radiation passed through the coating, disturbing a small region of the coating in a reproducible manner, again permitting or causing radiation to pass through the coating including the disturbed region and measuring the radiation passed through the disturbed coating, determining the change in the radiation passed through the coating as a result of the disturbance and indicating the change as the effect on the adherence of the coating to the surface of the reproducible disturbance and thence of the efficiency or otherwise of the apparatus of the coating.

The method may include repeating the said disturbance and measurement in turn at one position until the coating is removed from the surface, which may be indicated by repeated similar measurements of the radiation passing through the coating. The number of repeated such disturbances required to remove the coating can be an indication of the adherence of the coating.

Other routines may be used to determine the thickness of the powder layer. These can be calibrated absolutely by fusing the powder coating and measuring the resulting thickness. A metal strip may be included with the test piece and, after coating, have the coating fused to represent a coated product, the coating on the test-piece being assessed as described above for comparison with the fused coating.

The measurements may be repeated at another region of the coating.

The coating may be on a test-piece coated or in association with or attached to an article to be coated or may be on a test-portion of an article to be coated.

Figure 2:
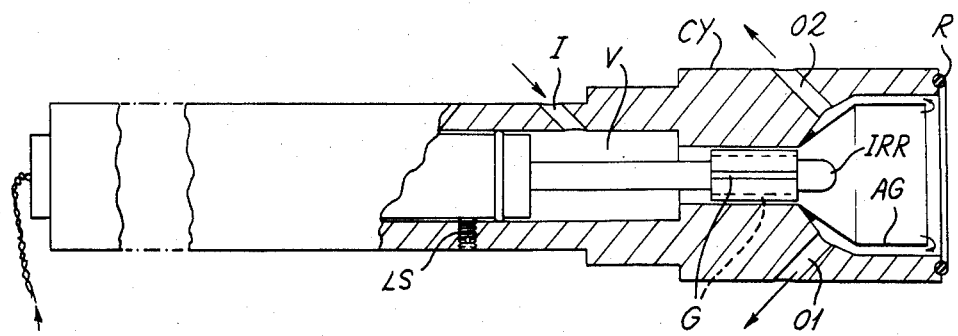

Embodiments of the invention will now be described with reference to the accompanying drawings which show:

in FIG. 1 a coated test piece and the assessment apparatus, and in FIG. 2 a probe for the apparatus is shown partly in cross-section.

In FIG. 1 a test piece substrate SG, conveniently of glass, has a conductive coating CC, which is conveniently produced by metallising. The substrate and conductive coating are arranged to be transmissive to a suitable radiation, such as infra-red. The conductive coating is shown as one surface only of the test-piece but it may be useful to coat both sides and possibly apply other than earth potential to the remote conductive coating to simulate actual powder deposition conditions.

By use of the coating technique and material to be assessed a coating, PC, of the material is deposited on the conductive coating, CC, which is generally earthed to approximate to the article to be actually coated. The coated test-piece is then subjected to the assessment apparatus. This includes a source of infra-red radiation, IRS, which may be coded, at say 25 KHz, to reduce interference from background radiation and a detector of infra-red radiation, IRD, opposed at opposite surfaces of the test-piece to send radiation therethrough and measure the amount sent through. The detector is associated with a fluid pressure duct FPD supplied from a source of fluid pressure, such as dry compressed air, through a valve FPV. The air is dry to avoid false results. A further fluid pressure supply duct FPC provides a small continuous flow of air to clean the viewing area of detector IRD and to disperse powder dislodged from the coating. The continuous supply tends to remove the powder upwardly by the upward inclination of the outlet FPO of supply duct PC. The detector and associated duct are surrounded and enclosed by a container CT such as a cylindrical tube, shown partly cut-away, about 25 mm in diameter which has a seal, TS, such as an O-ring, at the lower end to form a fluid-pressure-tight contact with the powder coating. The duct and detector are positioned in the container to maintain their positions in use. The tip of the duct FPD is maintained at a set distance from the end of the tube so that when placed on the powder coating a consistent arrangement is obtained. Typically the tip of the duct is between 5 mm and 30 mm and conveniently about 20 mm from the powder surface. The outlet FPO is positioned beneath the level of the tip of duct FPD. The powder dispersed by air from outlet FPO can leave the open top of container CT. The valve FPV is conveniently a small, fast-acting electropneumatic device, such as that available from Farnell Instruments, as in operation it is required to deliver pulses of fluid, such as compressed air, lasting for between some 100 milliseconds or less and a second or more in a repeatable manner and at a repetition rate of once every few seconds. The valve conveniently operates in about 1 to 5 milliseconds. The supply pressure is typically 0.3 to 1.0 bars above atmospheric pressure. The valve is conveniently a change-over type, venting air to waste except when a pulse is required.

The source of infra-red radiation and the detector are respectively energised and connected to signal processing circuitry in any suitable manner, as is well-known in the art, to provide an indication of the transmissivity of the powder coating on the substrate between the source and the detector. The exact manner in which the indication is used is discussed later.

In operation of the arrangement to assess the powder coating the powder coating on the substrate is introduced into the test apparatus and the container CT brought carefully into sealing engagement with the powder coating. A measurement of the transmissivity of the undisturbed coating is then made using the opposed infra-red source and detector. (It will be clear that the test apparatus ensures that these items are kept sufficiently well-aligned for consistent results.)

Fluid pressure control valve FPV is then operated to apply a short pulse of compressed air to disturb or dislodge powder from the surface. The transmissivity is again measured. This sequence of disturbance and measurement is repeated until a maximum value of transmissivity is reached indicating that all the powder has been displaced from beneath the duct tip. The number of pulses to a maximum value is noted. Ten to 50 pulses may be needed in a practical case, depending in part on the supply pressure.

The response of the powder coating to disturbance by different length and pressures of air pulse, measured by change in transmissivity, is thus shown as a series of values which can be compared with a series obtained for powder deposited in a different manner or powder from another batch deposited in the same manner to determine which technique is more effective or to check the consistency of the powder's properties from batch to batch.

The assessment technique can be refined by repeating the measurements at different places on a coating sample. For example on a sample 5 inches (125 mm) square 20 sets of measurements can be made without interference occurring. The measurements are conveniently supplied directly to and processed in a microcomputer and it is also possible to use such a microcomputer to control via the valve FPV the duration and pressure of the air pulse and the repetition rate and the number of pulses to produce a rapid test sequence to reduce the time to assess a coating. This can be important if the assessment is made during or as a preliminary to a production run. It may be possible to make tests every 2 or 3 seconds and to complete the 20 tests on a sample in 20 to 30 minutes, or less. The microcomputer can be used to process the measurements and by reference to stored information indicate whether or not a sample represents a better or worse coating technique. An undisturbed part of the powder coating can be fused to determine the thickness of coating produced.

A further arrangement embodying the invention will now be described with reference to FIG. 2. This arrangement is capable of making several assessments of a coated test piece automatically.

A test piece is formed by a glass plate with a metal coating as before. The plate is some 10 to 15 cm × 3 cm although the dimensions are not critical. A test piece carrier is formed of metal plate about 15 to 20 cm square. The metal plate has an I-shaped member attached to it. On each side of the I a test piece can be inserted into grooves and held with the metal coated surface of the test piece exposed for powder coating. Steel test plates can be held on the two cross-pieces of the I. These are fusing test pieces. The whole assembly of carrier with two glass and two steel plates can then be exposed to a powder coating process to be assessed. The coating will be reasonably uniform over the assembly so the quality of a fusing test piece coating when it is fused can be correlated with the coating assessment on the glass test pieces. Clearly other forms of test piece and carrier can be used.

The coating on a glass test piece can be assessed in an automated assessment device controlled by, for example, a microcomputer.

The automated device has a mechanised carrier for the test piece to hold it in a vertical plane and a mechanised probe carrying an assessment head similar to that in container CT in the drawing. The carrier is arranged to move the test piece lengthwise in its plane along a test path through a number of test positions while the probe can be moved horizontally towards and away from the test path to carry out an assessment when the test piece is in a test position. The whole device can be assembled in a small unit to include the associated electronics and be connected to a microcomputer.

A suitable operating cycle is for the automated device to "initialise" its readings in the absence of a test piece. The probe therefore emits a blast of air to expel any coating powder left in the probe from a previous test. A test piece is inserted. The probe is first quickly scanned over an inserted test piece to check "uniformity" of powder coating and then moved stepwise to carry out a series of assessments if the test-piece appears to have a reasonably uniform coating of powder.

When a test-piece, such as the plate just described, carrying a coating to be assessed is placed in the carrier, the probe is held back from the test path while the carrier is caused to move the test piece once to-and-fro past the probe. The probe, by measuring radiation transmission, but not blowing air, can determine whether or not the coating along the part of the test piece seen by the probe is sufficiently uniform to justify an assessment. This stage, particularly in a fully automatic sequence, avoids waste of time on badly coated or damaged test pieces.

If the test piece has a sufficiently uniform coating the assessment proper takes place. The carrier can be caused to step, by for example a stepper motor drive under the control of the microcomputer, through a number of test positions on the test path (spring return may be used if required). With a test piece of the approximate shape given, that is a length about four times the width, four positions are appropriate. The probe is of circular cross-section and has a diameter somewhat less than the width of the test piece.

At this point the detector probe is described in more detail. One possible form is as shown in FIG. 2. The main difference from the arrangement in FIG. 1 is that the transmitter of radiation is now in the cylinder associated with the air-blast while the receiver is behind the test piece. Either arrangement is effective and the choice can be made with regard to the form of the apparatus. An infra-red radiator IRR, such as a l.e.d., is held on the axis inside a cylinder CY so that air can be blown around the radiator device and out of the end of the cylinder. An O-ring R in the end of the cylinder can seal the end to the test piece. Air is supplied under pressure at inlet I in a suitable series of pulses. Powder disturbed by the air blown around the radiator device is extracted with this air which, when the cylinder end is closed, is exhausted with a venturi or similar action activated by air supplied in said series of pulses to entrain the powder through the cylinder wall at outlets O1, O2. The venturi is connected to outlets O1, O2 (one outlet only may be provided) and is supplied with air either from the pulsed supply to inlet I or another supply. The conical air guide AG, is sealed to cylinder CY so that air flowing through guides G is directed to the surface to be assessed to disturb and entrain powder before being exhausted by the action of the venturi. The arrows indicate the air path. Additional or alternative air supplies can be used to extract powder, for example a continuous flow can be applied to the venturi.

The exact form of construction of the probe can be varied to suit the form of the test device but successful and repeatable measurements have been made where the infra-red radiator device is mounted on the probe cylinder axis with air paths past the device such as grooves G or apertures. In one form the device is on a shaft along the cylinder axis so that it can be set in lengthwise position for optimum performance and air action and held by locking screw LS. The air is conveniently supplied to a volume V behind the radiator device and flows on through the grooves, which may be helical like rifling in a gun barrel. Instead of grooves an annular space all round the radiator device can be provided. Also some of the air can be diverted or directed to provide the powder extracting venturi action. The exact details can be settled by those skilled in the art to suit a particular arrangement but the significant points are described here.

The probe is arranged to be moved bodily lengthwise forward and backwards horizontally to engage and disengage the coated surface of a test piece. A solenoid drives the probe forward. Spring return can pull the probe backwards away from the test piece to allow movement of the test piece to the next position.

The radiation passing through the coated test piece is detected by a suitable device, e.g. a p.i.n. diode held fixed behind the test position. The diode is conveniently mounted in a tubular holder as a detector assembly to allow adjustment. The detector assembly preferably includes an iris to determine the field of view and a lens to focus the radiation on the diode. The iris limits the field of view to that part of the test piece where the air blast has uniform effect. In one example this part is about 5 mm in diameter. It has been found that the size and uniformity of the area affected depends on the form of the probe and the size, number and shape of the grooves, or other air path, past the radiator device is significant. The output of the detector is applied to a suitable receiver circuit to process the signal. To avoid background interference the radiation is conveniently infra-red modulated at about 25 KHz by a square wave. The square wave frequency is set by a "555" type oscillator using a polyester capacitor to produce a stable frequency. The receiver is tuned to 25 KHz by using a high pass input filter followed by a band pass filter. The filters are active filters to pass above 15 KHz and between 20 KHz and 30 KHz respectively. A precision rectifier and averaging circuit complete the receiver. Clearly other techniques may be used.

To recapitulate, the arrangement initialises the reading by cleaning the probe by blowing any remnant powder away, checks the uniformity of an inserted coated test piece and then steps the test piece through a number of positions.

At each position in turn of the test piece the probe comes forward and carries out a sequence of transmission measurements and air-blasts to assess the coating. A set of instructions to cause a microcomputer to operate the stepping motor and solenoid will be readily drawn up by one skilled in the art and no further description is needed. The action during each assessment is given in more detail. A closed loop of a compressed air supply, a pressure transducer and a pressure regulator is set up for the air supply to the probe. An on/off valve controls the supply of air at a regulated pressure to the probe. In one embodiment the air supply to disturb the coating and the air supply to extract powder are turned on and off at the same time, via a common feed. In another embodiment separately controlled feeds are used so that a continuous or other timing of powder extraction is usable. In operation of the control loop an analog of the air pressure value is supplied by the linear pressure transducer for comparison with a stored required value and any corrective action. The required value can be selected by an operator or can be deduced by the control instructions of the computer from results of earlier tests.

In one embodiment the transmissibility of the undisturbed coating is measured then the first pulse of air is applied and the transmissibility measured again. Further air pulses are applied and transmissivity measured, typically an air pulse is about 100 milliseconds long at an interval of a 100 or so milliseconds or more. The interval does not appear to be critical.

Various test regimes may be used. An effective regime is to repeat the air pulses until a steady transmissivity is measured. This is usually the cleared test piece. The number of pulses to reach this condition and the way the transmissivity rises to the steady value give information about the coating quality. Ten pulses usually provides such a steady result.

By repeating the assessment and comparing the results with the quality of the fused coating it is possible to establish for a given powder and coating technique (that is voltage and other conditions) what transmissivity characteristic indicates a proper coating action. In this way the behaviour of a coating line can be measured and monitored so that faulty coatings are not fused to articles. The speed of the assessment is such that little delay is needed to carry it out. A coated test piece can be examined as described above at four positions in a minute or less to provide a check on coating quality.

Various statistical and data handling techniques can be applied to the results of the assessment action to provide a basis for comparison, particularly for less-skilled users in a production environment where a go/-no-go result may be adequate. Curve fitting is one technique. As a research device variation of coating quality with coating conditions or coating technique can be assessed. In particular the effects of particle-to-particle adhesion and particle-to-substrate adhesion can be examined. Correlation between transmissibility and fused coating thickness is also found by employing the assessment technique embodying the invention.

The test piece of the form just described, with facility for fusing checks as well, can clearly be readily used in production line techniques by providing a branch of the production line by which the coated test piece is passed through an automated assessment station while the simultaneously coated articles are delayed a short while, such as a minute for example on a conveyor loop, until the coating quality is approved and fusing can take place. In this way considerable saving of material by the avoidance of fusing faulty coatings is possible.

As is known in the electrostatic powder coating art various techniques and materials are available but no quantitative assessment of the quality of a coating technique is available. The tests used at present are subjective and by rule-of-thumb and the effect of varying a parameter of the coating technique or the powder specifiction often impossible to determine with precision or even certainty. The amount of powder which is actually applied can now also be measured using the techniques described above, thus avoiding too thin or thick coatings during production. Using the assessment apparatus and method it is possible to examine the efficiency of the electrostatic coating equipment, the optimum coating parameters for different powders and the operating conditions for maximum powder adhesion. This is an addition to any information about the powder itself which is obtained by existing measurement of powder resistivity (electrical).

Tests using high voltage corona needles (of either polarity) and using low voltage corona needles, embedded in a body, with a grounded attractor electrode have shown that reliable assessment of the coating process is possible and optimum conditions for the powder and the operating voltage etc. can be determined. There is no reason to believe that similar results will not be obtained with the tribo-electric type or any other type of electrostatic coating process.

The above assessment techniques are thus effective to provide rapid measurements of coating quality by which the process can be made more efficient and consistent, leading to savings in material and improved yield of acceptable product.

We claim:

1. An apparatus for destructive assessment of a particulate coating including means to apply radiation to a deposited particulate coating and means to measure the radiation passed through the coating, means to disturb a small region of the particulate coating in a reproducible manner, means to measure the radiation passed through the disturbed coating, and means to determine the change in the radiation transmissibility of the deposited particulate coating as a result of the disturbance whereby an indication of the effect on the coating of the reproducible disturbance is provided as an indication of the adherence of the coating and the efficiency or otherwise and the deposition of the coating.

2. Apparatus according to claim 1 including means to repeat the disturbance at the already disturbed coating to permit a further such determination.

3. Apparatus according to claim 1 including a conductive surface connectable to ground and to which a coating or powder may be applied by electrostatic means, fluid pressure means to disturb said small region of the coating and means to send infra-red radiation through the coating and the surface, and any support therefor, to measure the change in the transmissivity of the coating resulting from the disturbance.

4. Apparatus according to claim 3 in which the conductive surface is a metallic coating on a glass support to form at test piece.

5. Apparatus according to claim 1 in which the means to disturb the coating is a fluid pressure duct, surrounded by a housing sealable to a coating and provided with a controllable source of fluid pressure, such as compressed air suppliable in bursts of set time and presure.

6. Apparatus according to claim 1 in which the means to apply radiation is a solid-state detector or transmitter of infra-red radiation associated with the fluid pressure duct and an opposed respective source or detector of said radiation.

7. Apparatus according to claim 1 arranged to pass the radiation normally or at another angle through the coating and any supporting surface and substrate, which surface and substrate are radiation-transmissive.

8. Apparatus according to claim 1 arranged to reflect the radiation, to pass twice through the coating for measurement, for an opaque substrate or supporting surface.

9. A method of assessing a particulate coating including applying a coating to a surface, permitting or causing radiation to pass through the coating and measuring the radiation passed through the coating, disturbing a small region of the coating in a reproducible manner, again permitting or causing radiation to pass through the coating including the disturbed region and measuring the radiation passed through the disturbed coating, determining the change in the radiation passed through the coating as a result of the disturbance and indicating the change as the effect on the adherence of the coating to the surface of the reproducible disturbance and thence of the efficiency or otherwise.

10. A method according to claim 9 including repeating the said disturbance and measurement in turn at one position until the coating is removed from the surface, which occurrence may be indicated by repeated similar measurements of the radiation passing through the coating.

11. A method according to claim 10 including assessing the number of repeated such disturbances required to remove the coating as an indication of the adherence of the coating.

12. A method according to claim 9 including another test routine to determine the thickness of the powder layer.

13. A method according to claim 12 including calibrating absolutely by fusing the powder coating and measuring the resulting thickness.

14. A method according to claim 11 in which a metal strip is included with the test piece and, after coating, has the coating fused to represent a coated product, and in which the coating on the test-piece is assessed for comparison with the fused coating.

* * * * *